(12) United States Patent
Salarian et al.

(10) Patent No.: US 8,876,739 B2
(45) Date of Patent: Nov. 4, 2014

(54) SYSTEM FOR CLINICAL ASSESSMENT OF MOVEMENT DISORDERS

(75) Inventors: Arash Salarian, Zurich (CH); Fay Horak, Portland, OR (US); Kamiar Aminian, Le Tour-de-Peilz (CH)

(73) Assignee: Oregon Health & Science University, Portland, OR (US)

( * ) Notice: Subject to any disclaimer, the term of this patent is extended or adjusted under 35 U.S.C. 154(b) by 475 days.

(21) Appl. No.: 12/842,843

(22) Filed: Jul. 23, 2010

(65) Prior Publication Data
US 2011/0092860 A1     Apr. 21, 2011

Related U.S. Application Data

(60) Provisional application No. 61/228,326, filed on Jul. 24, 2009.

(51) Int. Cl.
*A61B 5/11* (2006.01)
*A61B 5/00* (2006.01)

(52) U.S. Cl.
CPC .............. *A61B 5/4023* (2013.01); *A61B 5/6828* (2013.01); *A61B 5/681* (2013.01); *A61B 5/6831* (2013.01)
USPC ....................................................... 600/595

(58) Field of Classification Search
USPC .................................................. 600/587, 595
See application file for complete search history.

(56) References Cited

U.S. PATENT DOCUMENTS

| | | | | |
|---|---|---|---|---|
| 8,092,398 | B2 * | 1/2012 | Weinberg et al. | 600/595 |
| 2004/0015103 | A1 * | 1/2004 | Aminian et al. | 600/595 |
| 2007/0032748 | A1 * | 2/2007 | McNeil et al. | 600/595 |
| 2011/0213275 | A1 * | 9/2011 | Boos et al. | 600/595 |

OTHER PUBLICATIONS

Higashi et al. "Quantitative Evaluation of Movement Using the Timed Up-and-Go Test" IEEE Engineering in Medicine and Biology Magazine Jul. 2008.*

* cited by examiner

*Primary Examiner* — Sean Dougherty
*Assistant Examiner* — Michael C Stout
(74) *Attorney, Agent, or Firm* — Schwabe, Williamson & Wyatt (57) ABSTRACT

According to one embodiment of the present invention, the system for clinical assessment of movement disorders (iTUG) is comprised of a) a protocol to assess gait, balance, and mobility; b) a plurality of wearable sensors including accelerometers, gyroscopes, magnetometers, optical sensors, and goniometers to record kinematics data obtained from a patient during said protocol; c) means for wirelessly transmitting said kinematics data to a storage and data processing server; and d) a plurality of statistical and biomedical signal processing methods to analyze said kinematic data and derive a plurality of metrics (outcomes) to objectively quantify movement disorders. A specially important outcome for the assessment of movement disorders is described, namely, the quantification of the onset and offset parameters during turning. A method for quantification of said onset and offset turning parameters involves 1) collecting data to measure the angle of the trunk during turning, 2) modeling said angle using a mathematical model, and 3) using numerical optimization and estimation methods for fitting the model in the data to determine said onset and offset turning parameters.

14 Claims, 13 Drawing Sheets

| Activity | Parameter | PD Mean | PD S.D. | Control Mean | Control S.D. | rank-sum p-value |
|---|---|---|---|---|---|---|
| Gait | | | | | | |
| Temporal | Cadence (steps/min) | 111.1 | 6.2 | 120.4 | 7.6 | 0.0061 |
| | Stance (%) | 58.9 | 1.6 | 59.4 | 2.4 | 0.2366 |
| | Double Support (%) | 17.8 | 3.1 | 18.8 | 4.9 | 0.2366 |
| | Limp (%) | 2.3 | 1.1 | 2.1 | 1.2 | 0.6236 |
| Lower Limbs | RoM-Shank (°) | 69.6 | 7.3 | 69.6 | 7.0 | 0.8852 |
| | RoM-Thigh (°) | 43.7 | 5.7 | 43.4 | 3.8 | 0.6650 |
| | RoM-Knee (°) | 54.6 | 6.7 | 56.0 | 7.3 | 0.5444 |
| | Stride-Length (%h) | 75.6 | 7.6 | 74.8 | 5.8 | 0.7508 |
| | Stride-Velocity (%h/s) | 70.3 | 9.7 | 75.0 | 7.2 | 0.1939 |
| | Peak Swing Velocity (°/s) | 333.5 | 47.1 | 359.8 | 43.6 | 0.2602 |
| Upper Limbs | Arm-Swing Pitch (°) | 17.6 | 4.3 | 24.0 | 10.6 | 0.0783 |
| | Arm-Swing Yaw (°) | 28.9 | 9.8 | 39.4 | 13.1 | 0.0464 |
| | Peak Arm Swing Velocity (°/s) | 123.2 | 32.0 | 174.0 | 50.4 | 0.0051 |
| | Arm Swing Speed Asym (%) | 36.3 | 17.9 | 23.1 | 12.4 | 0.0531 |
| Trunk | Peak Trunk Horiz. Velocity (°/s) | 34.7 | 9.0 | 44.2 | 10.1 | 0.0226 |
| | Peak Trunk Sagit. Velocity (°/s) | 30.7 | 6.9 | 38.4 | 9.2 | 0.0783 |
| | RoM-Trunk Horiz (°) | 7.7 | 2.4 | 8.8 | 1.4 | 0.1260 |
| | RoM-Turnk Sagit (°) | 4.4 | 0.7 | 4.7 | 0.7 | 0.4705 |
| Turning | | | | | | |
| Trunk | Peak Angular Velocity (°/s) | 162.3 | 30.85 | 172.44 | 30.13 | 0.7950 |
| | Duration (s) | 2.18 | 0.43 | 1.79 | 0.27 | 0.0226 |
| Lower Limbs | Steps | 4.08 | 1.00 | 3.50 | 0.52 | 0.1422 |
| | Average Step Time (s) | 0.57 | 0.07 | 0.56 | 0.07 | 0.7508 |
| | Max Step Time (s) | 0.71 | 0.15 | 0.69 | 0.12 | 0.7507 |
| | Last Step Time Before Turn (s) | 0.56 | 0.04 | 0.52 | 0.04 | 0.0302 |
| | Number of Double Steps | 0.33 | 0.49 | 0.00 | 0.00 | 0.0357 |
| Sit-to-Stand | | | | | | |
| Trunk | Peak Angular Velocity (°/s) | 89.13 | 17.20 | 92.69 | 15.77 | 0.8399 |
| | Average Angular Velocity (°/s) | 29.43 | 3.22 | 30.81 | 3.85 | 0.3123 |
| | Duration (s) | 2.18 | 0.25 | 2.10 | 0.26 | 0.4178 |
| | RoM-Trunk (°) | 37.11 | 3.11 | 37.49 | 6.22 | 0.8399 |
| Turn-to-Sit | | | | | | |
| Trunk | Duration (s) | 2.96 | 0.68 | 2.40 | 0.33 | 0.0226 |
| | RoM-Trunk (°) | 29.22 | 3.80 | 30.20 | 6.01 | 0.9770 |
| Lower Limbs | Steps | 3.00 | 0.85 | 3.17 | 1.34 | 1.0000 |
| | Average Step Time (s) | 0.72 | 0.17 | 0.55 | 0.16 | 0.0304 |
| | Max Step Time (s) | 1.08 | 0.41 | 0.77 | 0.34 | 0.0734 |
| | Last Step Time Before Turn (s) | 0.56 | 0.04 | 0.52 | 0.04 | 0.0375 |
| | Number of Double Steps | 0.00 | 0.00 | 0.08 | 0.29 | 0.3593 |

FIG. 9

| Activity | Parameter | Test1 Mean | Test1 S.D. | Test2 Mean | Test2 S.D. | ICC(1,1) ρ | 95% CI bounds of ICC Lower | 95% CI bounds of ICC Upper |
|---|---|---|---|---|---|---|---|---|
| Gait | | | | | | | | |
| Temporal | Cadence (steps/min) | 116.38 | 8.85 | 114.61 | 9.17 | 0.94 | 0.84 | 0.98 |
| | Stance (%) | 58.89 | 2.10 | 59.29 | 2.14 | 0.92 | 0.79 | 0.97 |
| | Double Support (%) | 17.78 | 4.19 | 18.58 | 4.27 | 0.92 | 0.79 | 0.97 |
| | Limp (%) | 2.02 | 0.91 | 2.13 | 1.10 | 0.25 | -0.23 | 0.64 |
| Lower Limbs | RoM-Shank (°) | 72.39 | 8.78 | 71.72 | 7.39 | 0.64 | 0.26 | 0.85 |
| | RoM-Thigh (°) | 45.23 | 4.92 | 44.47 | 5.12 | 0.63 | 0.25 | 0.85 |
| | RoM-Knee (°) | 55.79 | 8.99 | 54.20 | 7.41 | 0.55 | 0.12 | 0.81 |
| | Stride-Length (%h) | 79.37 | 8.25 | 78.53 | 7.05 | 0.67 | 0.30 | 0.86 |
| | Stride-Velocity (%h/s) | 76.98 | 9.52 | 75.26 | 9.82 | 0.78 | 0.51 | 0.92 |
| | Peak Swing Velocity (°/s) | 364.24 | 56.25 | 355.89 | 54.26 | 0.78 | 0.50 | 0.91 |
| Arm Swing | RoM- Arm Pitch (°) | 21.83 | 11.02 | 21.31 | 9.36 | 0.68 | 0.32 | 0.87 |
| | RoM Arm Yaw (°) | 31.92 | 12.30 | 33.47 | 13.68 | 0.84 | 0.62 | 0.94 |
| | Peak Velocity (°/s) | 147.41 | 49.07 | 146.98 | 53.99 | 0.90 | 0.75 | 0.96 |
| | Speed Asym (%) | 34.24 | 17.38 | 34.03 | 17.82 | 0.94 | 0.85 | 0.98 |
| Trunk | Horiz. Velocity (°/s) | 40.06 | 11.97 | 39.67 | 12.13 | 0.95 | 0.86 | 0.98 |
| | Sagit Velocity (°/s) | 37.65 | 11.83 | 34.65 | 10.97 | 0.83 | 0.61 | 0.94 |
| | RoM-Trunk Horiz (°) | 7.97 | 2.26 | 8.26 | 2.42 | 0.78 | 0.50 | 0.91 |
| | RoM-Turnk Sagit (°) | 4.72 | 1.26 | 4.46 | 0.73 | 0.52 | 0.08 | 0.79 |
| Turning | | | | | | | | |
| Trunk | Peak Angular Velocity (°/s) | 164.88 | 33.27 | 159.61 | 31.79 | 0.86 | 0.67 | 0.95 |
| | Duration (s) | 2.01 | 0.52 | 1.99 | 0.41 | 0.89 | 0.74 | 0.96 |
| Lower Limbs | Steps | 4.00 | 0.94 | 3.82 | 0.88 | 0.75 | 0.45 | 0.90 |
| | Average Step Time (s) | 0.58 | 0.09 | 0.59 | 0.07 | 0.61 | 0.21 | 0.84 |
| | Max Step Time (s) | 0.73 | 0.22 | 0.71 | 0.13 | 0.50 | 0.05 | 0.78 |
| | Step Before Turn (s) | 0.54 | 0.04 | 0.54 | 0.05 | 0.85 | 0.64 | 0.94 |
| | # of Double Steps | 0.18 | 0.39 | 0.18 | 0.39 | 0.22 | -0.27 | 0.62 |
| Sit-to-Stand | | | | | | | | |
| Trunk | Peak Angular Velocity (°/s) | 92.07 | 24.32 | 91.71 | 18.59 | 0.43 | -0.04 | 0.75 |
| | Average Angular Velocity (°/s) | 29.65 | 4.54 | 30.15 | 3.87 | 0.22 | -0.27 | 0.62 |
| | Duration (s) | 2.20 | 0.26 | 2.12 | 0.26 | 0.04 | -0.42 | 0.50 |
| | RoM-Trunk (°) | 36.73 | 4.64 | 36.98 | 5.02 | 0.22 | -0.27 | 0.62 |
| Turn-to-Sit | | | | | | | | |
| Trunk | Duration (s) | 2.59 | 0.53 | 2.77 | 0.67 | 0.84 | 0.61 | 0.94 |
| | RoM-Trunk (°) | 32.35 | 8.38 | 30.75 | 5.96 | 0.77 | 0.47 | 0.91 |
| Lower Limbs | Steps | 2.82 | 0.53 | 3.00 | 0.94 | 0.23 | -0.26 | 0.63 |
| | Average Step Time (s) | 0.62 | 0.14 | 0.67 | 0.16 | 0.52 | 0.08 | 0.79 |
| | Max Step Time (s) | 0.78 | 0.33 | 0.97 | 0.39 | 0.38 | -0.10 | 0.72 |
| | Last Step Time Before | 0.53 | 0.04 | 0.54 | 0.05 | 0.78 | 0.50 | 0.91 |

FIG. 10

| GAIT PARAMETERS | Untreated PD Mean ± SE | Control Mean ± SE | p-value | AUC |
|---|---|---|---|---|
| Upper Body | | | | |
| Peak Arm Velocity | 124.4 ± 9.2 | 187.5 ± 10.9 | <0.001 | 0.910 |
| Peak Arm Velocity (MAS) | 103.4 ± 10.6 | 187.5 ± 10.9 | <0.001 | 0.958 |
| Peak Arm Velocity (LAS) | 145.4 ± 13.7 | 187.5 ± 10.9 | 0.025 | 0.764 |
| Arm Swing Range of Motion (deg) | 29.2 ± 2.8 | 42.3 ± 3.2 | 0.005 | 0.826 |
| Arm Swing Range of Motion (MAS) | 22.6 ± 2.9 | 42.3 ± 3.2 | <0.001 | 0.910 |
| Arm Swing Range of Motion (LAS) | 35.7 ± 4.9 | 42.3 ± 3.2 | 0.266 | 0.660 |
| Arm Swing Asymmetry (% lv) | 35.5 ± 5.4 | 21.6 ± 2.7 | 0.031 | 0.708 |
| Lower Body | | | | |
| Cadence (steps/min) | 111.7 ± 1.7 | 121.2 ± 2.1 | 0.001 | 0.854 |
| Stride Velocity (%ht/sec) | 71.0 ± 2.8 | 77.8 ± 2.0 | 0.065 | 0.729 |
| Stride Velocity (MAS) | 71.0 ± 2.9 | 77.8 ± 2.0 | 0.071 | 0.715 |
| Stride Velocity (LAS) | 71.0 ± 2.8 | 77.8 ± 2.0 | 0.063 | 0.729 |
| Stride Length (%ht) | 76.0 ± 2.2 | 76.9 ± 1.4 | 0.752 | 0.507 |
| Double Support Time (% gc) | 17.5 ± 0.9 | 18.9 ± 1.4 | 0.437 | 0.333 |
| Stride Time Variability (%) | 2.8 ± 0.3 | 2.9 ± 0.6 | 0.870 | 0.590 |
| Stride Length Variability (%) | 2.5 ± 0.1 | 3.2 ± 0.7 | 0.363 | 0.535 |
| Trunk | | | | |
| Peak Trunk Rotation Velocity (deg/sec) | 34.0 ± 2.6 | 44.6 ± 9.6 | 0.010 | 0.806 |
| Trunk Rotation Range of Motion (deg) | 7.3 ± 0.7 | 9.2 ± 0.5 | 0.041 | 0.764 |
| TURNING PARAMETERS | | | | |
| Average Turning Velocity (deg/sec) | 76.2 ± 4.0 | 87.5 ± 3.2 | 0.037 | 0.764 |
| Peak Turning Velocity (deg/sec) | 163.3 ± 8.9 | 175.9 ± 8.3 | 0.312 | 0.617 |
| SIT-TO-STAND PARAMETERS | | | | |
| Average Sit-to-Stand Velocity (deg/sec) | 30.9 ± 1.0 | 34.1 ± 2.1 | 0.199 | 0.618 |
| Peak Sit-to-Stand Velocity (deg/sec) | 89.2 ± 4.9 | 94.1 ± 5.0 | 0.421 | 0.562 |

FIG. 11

| GAIT | UPDRS Motor Score | | UPDRS Bradykinesia | | UPDRS Gait/Posture | | UPDRS Rigidity | |
|---|---|---|---|---|---|---|---|---|
| Upper Body parameters | r | p-value | r | p-value | r | p-value | r | p-value |
| Arm Swing Range of Motion (deg) | -0.58 | 0.04 | 0.49 | 0.09 | -0.40 | 0.18 | -0.08 | 0.79 |
| Peak Arm Swing Velocity (deg/sec) | -0.62 | 0.02 | 0.49 | 0.10 | -0.50 | 0.09 | -0.18 | 0.57 |
| Arm Swing Asymmetry (% lv) | -0.34 | 0.27 | 0.53 | 0.07 | 0.23 | 0.45 | 0.05 | 0.86 |
| Trunk parameters | | | | | | | | |
| Trunk Rotation Range of Motion (deg) | -0.02 | 0.94 | 0.06 | 0.84 | 0.01 | 0.97 | -0.50 | 0.09 |
| Peak Trunk Rotation Velocity (deg/sec) | -0.22 | 0.49 | 0.14 | 0.65 | -0.17 | 0.58 | -0.68 | 0.01 |
| Lower Body parameters | | | | | | | | |
| Cadence (steps/min) | -0.58 | 0.04 | 0.49 | 0.10 | -0.26 | 0.40 | -0.52 | 0.08 |
| TURNING | | | | | | | | |
| Average Turning Velocity (deg/sec) | -0.73 | 0.006 | 0.65 | 0.02 | -0.71 | 0.009 | -0.39 | 0.20 |

SYSTEM FOR CLINICAL ASSESSMENT OF MOVEMENT DISORDERS

CROSS REFERENCE TO RELATED APPLICATIONS

The present application claims priority to U.S. Patent Application No. 61/228,326, filed Jul. 24, 2009, entitled "System for Clinical Assessment of Movement Disorders," the entire disclosure of which is hereby incorporated by reference in its entirety.

GOVERNMENT INTERESTS

This invention was made with Government support under Grant/Contract No. 5R37AG006457-23 awarded by The National Institutes of Health (NIA: AG006457). The Government has certain rights in the invention.

TECHNICAL FIELD

This invention relates to methods and apparatus for assessment of movement disorders. Specifically, it relates to methods for obtaining quantitative outcomes for gait and postural transitions that are relevant for testing patients with balance and gait deficits as well as a neurological and musculoskeletal constraints.

BACKGROUND

Current methods for assessing improvement in movement disorders in clinical trials and clinical practice are insensitive, qualitative, offer limited reliability and repeatability, and require a large number of subjects. Many patients have gait and balance resulting in high fall risk, but clinicians have no practical method to objectively measure these responses for either clinical trials or clinical practice. Postural transitions such as rising from a chair and turning are particularly difficult for people with movement disorders such as Parkinson's disease or the frail elderly. The most commonly used test of fall risk from problems with postural transitions and slow gait is the Get Up and Go test (clinical TUG).

The Timed Up and Go test (TUG) is a widely used clinical test to evaluate balance and mobility. The TUG test uses a stop-watch to time how long it takes a subject to stand up from a chair, walk 3 meters, turn 180 degrees, walk back to the chair and sit down. The TUG test has been shown to predict falls in the elderly, reflect balance deficits and correlate with severity of moderate-to-severe Parkinson's disease. The clinical utility of the TUG is probably due to sequencing several mobility skills, such as turning and sit to stand transitions that require balance control, as well as straight-ahead gait.

The traditional TUG is limited, however, because performance is rated only by a single, total duration score from a stop-watch, so that it is not possible to determine which balance or gait subcomponent of performance are affected. Recently, researches have used a stop-watch to measure the duration of each of the four subcomponents of the TUG, namely sit-to-stand, gait, turning and turn-to-sit. However, using a stop-watch to find exact time of a rapid sequence of activities is difficult. To address this issue, a recent study used inertial sensors to measure the duration of each subcomponent of the TUG test automatically.

An important step needed to build a complete system to analyze all subcomponents of the TUG test is to analyze 180° turns. A difficulty in analyzing turning is defining the onset and offset of turns. Researchers have used angular velocity in the yaw-axis and a fixed threshold to define onset and offset of turning. A problem with fixed thresholds is that their exact value is hard to justify, may be dependent on the population, and tends to be influenced by noise and movement artifacts.

Besides providing detailed assessment of subjects' performance, a useful movement analysis system should be reliable. The TUG, itself, is a reliable test and a recent study has shown good test-retest reliability for the duration of its subcomponents. A useful clinical assessment tool also needs to be sensitive to pathology. While it is known that patients with advanced stages of Parkinson's disease (PD) show impaired motor performance compared to control subjects, it is difficult to identify mobility deficits in very early stages of their disease.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 9 shows a table containing sample iTUG outcome results grouped by type of activity.

FIG. 10 shows a table containing sample test-retest reliability of the proposed iTUG metrics.

FIG. 11 shows a table containing the gait and postural transition parameters obtained with the proposed iTUG test.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

This disclosure relates to methods and apparatus for assessment of movement disorders. Specifically, it relates to methods for obtaining quantitative outcomes for gait and postural transitions that are relevant for testing patients with balance and gait deficits as well as a neurological and musculoskeletal constraints. In exemplary embodiments, a computing device may be endowed with one or more components of the disclosed apparatuses and/or systems and may be employed to perform one or more methods as disclosed herein.

Figure 1:
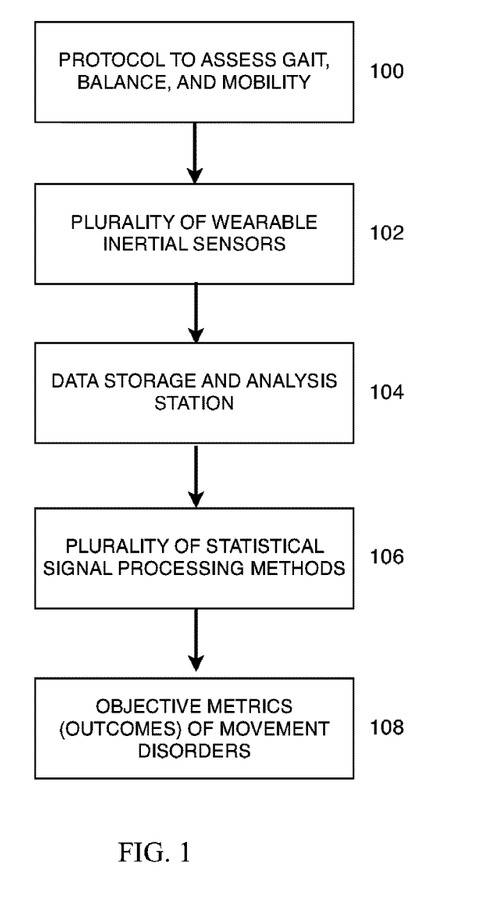
FIG. 1 shows a block diagram illustrating an embodiment.

FIG. 1 shows a block diagram illustrating an embodiment. According to one embodiment, the system for clinical assessment of movement disorders (iTUG) is comprised of a) a protocol 100 to assess gait, balance, and mobility; b) a plurality of wearable sensors 102 including accelerometers, gyroscopes, magnetometers, optical sensors, and goniometers to record kinematics data obtained from a patient during said protocol; c) means for transmitting said kinematics data to a storage and data processing server 104; and d) a plurality of statistical and biomedical signal processing methods 106 to analyze said kinematics data and derive a plurality of metrics (outcomes) 108 to objectively quantify movement disorders.

According to one embodiment the protocol to assess gait, balance, and mobility is substantially equivalent to the TUG protocol. According to this embodiment the protocol is divided into 4 major components: sit-to-stand, turn-to-sit, gait and turning. In this embodiment, and without limitation, the length of the normal TUG is extended from 3 meters to 7 meters to increase the total number of analyzable gait-cycles. Other embodiments employ other protocols designed to help clinically assess gait, balance, and mobility.

Figure 2:
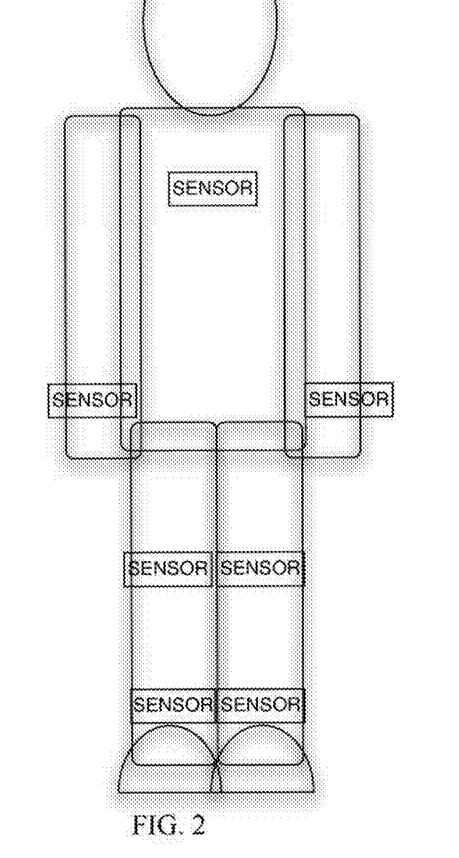
FIG. 2 illustrates the placement of wearable sensors according to one embodiment.

Each subcomponent of the protocol is detected with a unique subset of sensors: sit to stand and turn to sit transitions are detected and analyzed using the trunk sensor. Steps during gait and turns are detected using the two sensors on the shanks. Turns are detected using the trunk sensor. According to one embodiment the plurality of sensors includes wearable sensors are attached on the forearms, shanks, thighs, and sternum. Wearable sensors may include accelerometers, gyroscopes, magnetometers, optical sensors, and goniometers. FIG. 2 illustrates the placement of the inertial sensors according to one embodiment. To limit the number of recorded channels, a different combination of accelerometers and gyroscopes can be used for each body site. As an example, and without limitation, a sensor with a 3D accelerometer ($\pm$5 g) and a 2D gyroscope ($\pm$400°/s, yaw and pitch axes) can be fixed on sternum. A 2D gyroscope ($\pm$1200°/s, yaw and pitch axes) can be attached on each forearm and a single axis gyroscope ($\pm$600°/s, pitch axes) can placed on each thigh and shanks. Other sensor configurations can be used including 3D inertial sensors with specification exceeding those listed herein. According to one embodiment the sensors include means for transmitting the kinematics data recorded to a storage and data processing server. For instance, the sensors include an industry standard communication protocol such as Bluetooth, ZigBEE, WiFi, or radio frequency communications.

Figure 3:
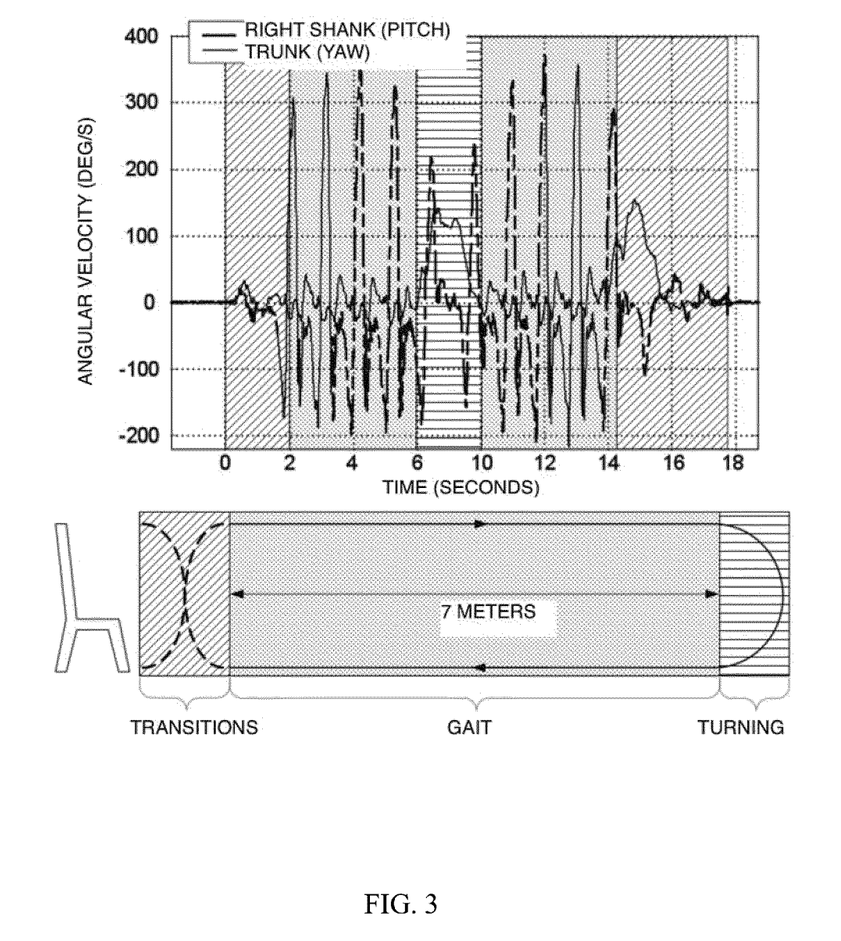
FIG. 3 shows the components of the proposed iTUG protocol and representative raw signals from angular velocity of a shank and sternum according to one embodiment.

According to one embodiment, the iTUG system includes a plurality of statistical and signal processing algorithms to analyze said kinematics data and derive a plurality of metrics (outcomes) to objectively quantify movement disorders. These outcomes include sit-to-stands metrics, gait metrics, turning metrics, and turn-to-sit metrics. Sit-to-stand metrics may include: a) Average and peak angular velocity of trunk in the sagittal plane (in degrees per second). B) Duration (in seconds) and range of motion of the trunk in the sagittal plane (in degrees). Gait metrics include: A) Temporal parameters including Cadence (number of steps per minute), Stance (as percentage of gait cycle time), Double support (as percentage of gait cycle time), Limp (i.e. difference between initial and terminal double support as a percentage of gait cycle time). B) Performance of the lower limbs including Range of Motion (ROM) of shanks, thighs as well as flexion-extension of knee (all in degrees), stride-length (normalized to the stature), stride-velocity (stride-length divided by gait cycle time) and peak angular velocity of shanks (in degrees per second). C) Performance of the upper limbs including arm-swing in Pitch and Yaw axes (in degrees), peak angular velocity (by combining Pitch and Yaw axes, reported in degrees per second) and its left/right asymmetry (difference of the left and right divided by the faster one, reported as percentage). D) Performance of the trunk including ROM in horizontal and sagittal planes as well as peak angular velocity in horizontal and sagittal planes. Turning metrics include: A) Duration of turns (in seconds). B) Peak angular velocity of the trunk in horizontal plane (in degrees per seconds). C) Number of steps, average step time (from heal-strike to heal-strike, in seconds), time for the longest step (in seconds), last step time right before turn (in seconds) and number steps of double steps, i.e.

successive steps with the same foot. Turn-to-sit metrics include: A) Turning metrics. B) Range of motion of trunk in the sagittal plane (in degrees). FIG. 3 shows the components of the proposed iTUG protocol and representative raw signals from angular velocity of a shank and sternum according to one embodiment.

Figure 13:
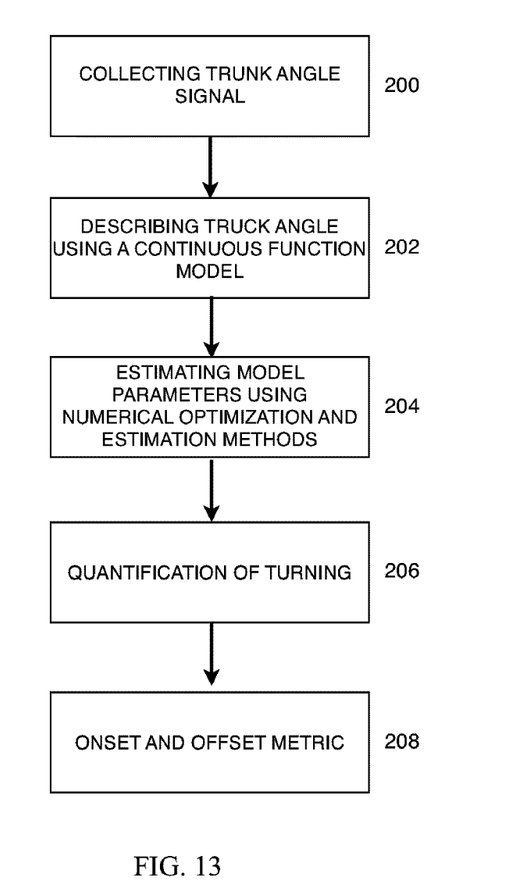
FIG. 13 shows a block diagram of the method to analyze turning and derive clinical outcomes.

According to one embodiment a critical outcome for the assessment of movement disorders is based on the quantification of the onset and offset parameters during turning. A method for quantification of said onset and offset turning parameters involves 1) collecting data to directly or indirectly measure the angle of the trunk during turning 200, 2) modeling said angle using a mathematical model 202, and 3) using numerical optimization methods for fitting the model in the data 204 in order to quantify said turning 206 and determining said onset and offset turning parameters 208. Sensor placement includes anywhere on trunk including sternum. Metrics may include peak velocity, mean velocity, and ROM during turning.

Figure 5:
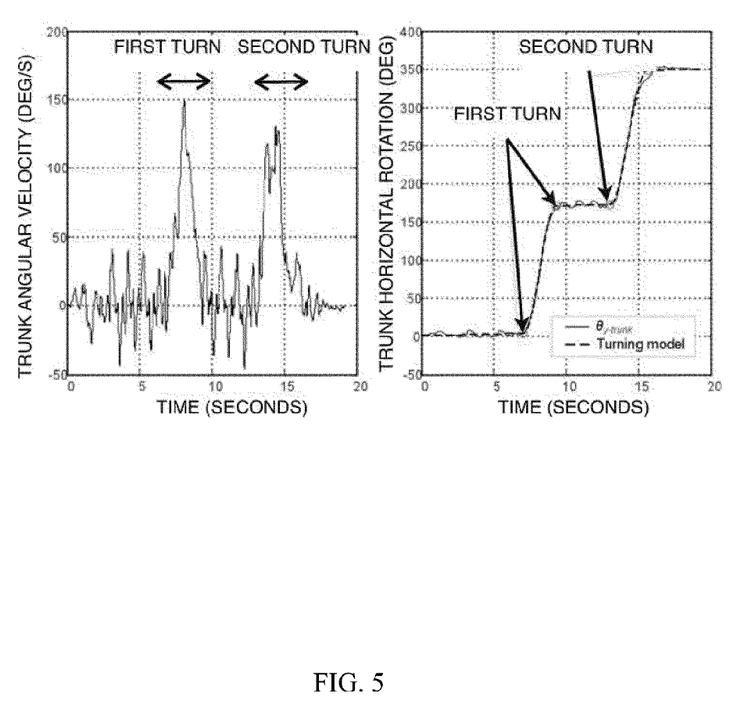
FIG. 5 shows the raw signal of the yaw gyroscope on the trunk during iTUG. The first peak corresponds to 180 degree turn and the second peak corresponds to the turn-to-sit transition and the relative angle of the trunk in the horizontal plane and fitted mathematical model.

According to one embodiment the analysis of turning is performed according to the following signal processing method designed to quantify the onset and offset of the turns. iTUG includes two 180° turns: one after walking a predetermined distance (e.g. 7 meters) and a turn-to-sit transition. Unlike initial and terminal contacts in gait analysis, onset and offset of turns are not time events marked by sudden, distinct movements of the body or impacts with the floor, but are rather a slow transition from one form of activity (gait) to another (turn). Researches have defined onset and offset of turns by setting a fixed threshold on the trunk angular velocity in the yaw axis. However, gait and transitions produce noticeable spurious signals in yaw angular velocity. As a result threshold-based methods are sensitive to noise and will probably have low reliability, especially with slow gait and turning speeds. This embodiment uses a mathematical model to find these transitions from straight to curved walking and back to straight walking (or sitting at the end of TUG) using an optimization method. To detect 180° turns, the signal is analyzed from the yaw gyroscope on the sternum $\omega_y(t)$ as shown in FIG. 5. This raw signal shows large variations associated with shoulder girdle rotation during walking. As seen in the raw signal, although it is relatively easy to identify when turns occurred in this signal, due to marked peaks in yaw velocity amplitude, it is difficult to see exactly where turns begin and end. After integrating $\omega_y(t)$ signal, the relative trunk angle in the horizontal plane $\theta y(t)$ is obtained. Since the initial angle of the trunk at the beginning of recording is unknown, a value of zero can be assumed. Thus, $\theta y(t)$ indicates how much the trunk was turned to the left or right relative to the beginning of the test. As seen in FIG. 5, walking components appear in $\theta y(t)$ as nearly flat lines with some variations due to yaw rotation oscillations of trunk. Turning components appear as positive or negative ramps, depending on the direction of turns. Since the sensor attached on the trunk could have a small inclination relative to the horizontal plane due to anatomy of this part of the body, differences in $\theta y(t)$ before and after turns could be smaller than 180°. According to one embodiment, a continuous mathematical model is used to describe $\theta y(t)$ during the iTUG protocol:

$$M(t) = a_1 E\left(\frac{t-b_1}{c_1}\right) + a_2 E\left(\frac{t-b_2}{c_2}\right) + C \cdot t \quad (1)$$

where $E(t)$ is a continuous piecewise function changing smoothly between two levels: $E(t)=-\frac{1}{2}$ if $t\geq\frac{1}{2}$, $E(t)=-\frac{1}{2}\sin(\pi t)$ if $-\frac{1}{2}\leq t\leq\frac{1}{2}$, and $E(t)=-\frac{1}{2}$ if $t\geq\frac{1}{2}$. In $M(t)$ drift and offset of the gyroscopes is assumed to be constant during the short period of iTUG and is described as constant slope C. In this model $\{a_1, b_1, c_1\}$ describe the first turn and $\{a_2, b_2, c_2\}$ describe the second turn. The $\{a_i, b_i, c_i\}$ coefficients used to estimate the amplitude of the turns (usually near, but less than, 180° due to sensors inclination), the time and duration of turns, respectively. In this model, period of the turns are defined as $$\left[b_i - \frac{c_i}{2}, b_i + \frac{c_i}{2}\right].$$

Figure 4:
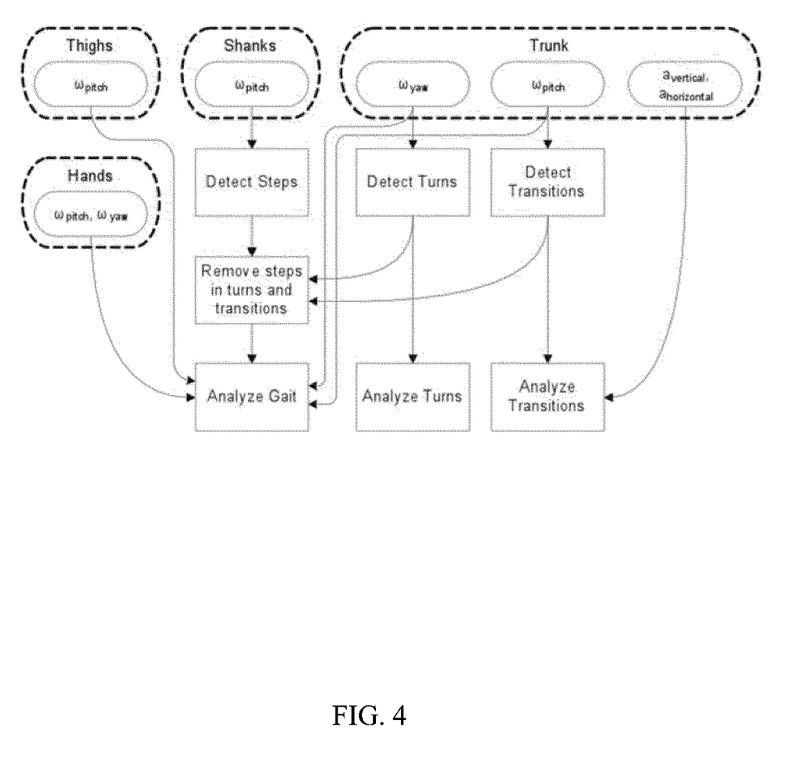
FIG. 4 shows a block diagram of the how wearable sensors can be used for the iTUG analysis algorithms according to one embodiment.

A subspace trust-region based, nonlinear, least squares optimization method is use to fit $M(t)$ on $\theta y(t)$. According to one embodiment, coefficient of determination R2 is used to evaluate the quality of model fit to data. According to alternative embodiments, similar mathematical models are used to accurately describe By (t) during the iTUG protocol. FIG. 4 shows a block diagram of the how inertial sensors can be used for the iTUG analysis algorithms according to one embodiment. FIG. 5 shows the raw signal of the yaw gyroscope on the trunk during iTUG. The first peak corresponds to 180 degree turn and the second peak corresponds to the turn-to-sit transition and the relative angle of the trunk in the horizontal plane and fitted mathematical model. Note that other mathematical models may also be used including the set of continuous functions, the set of continuous functions that are differentiable, nonlinear functions, nonparametric models, and non-differentiable models like a segmented line mode.

While particular embodiments have been described, it is understood that modifications and generalizations will be apparent to those skilled in the art without departing from the spirit of the invention.

1. Experimental Test Results.

The sections below describe an actual reduction to practice of one embodiment and the results obtained that demonstrate the embodiment performs its indented function and achieves superior sensitivity and repeatability results compared to prior art methods and apparatus.

1.1. Subjects

Twelve patients with idiopathic Parkinson's disease and 12 control subjects participated in this study. The two groups were age matched (60.4±8.5 vs. 60.2±8.2 years old). There were seven males in the PD group and three males in the control group. Healthy control subjects were either spouses of the patients or recruited from the community. Patients were in early-to-moderate stage of disease (H&Y score between 1 and 2.5, UPDRS motor score 20.0±9.4) and have never taken anti-Parkinsonian medications. Subjects were excluded if they had any neurological disorders other than PD, orthopedic disorders or other impairments that could potentially interfere with gait, or if they used orthotic devices or had artificial joints. All participants provided informed consent approved by the Oregon Health & Sciences Institutional Review Board.

1.2. Measurement Protocol

Subjects performed a Get-up and go (TUG) test 3 times. They all used an armless chair and were instructed to not to use their arms to stand up. The beginning and end of a 7-meter pathway were clearly marked with 0.5-inch tape on the floor. These markings were shown to the subjects before the test. The end line was 3 meters away from the wall. Subjects were instructed to sit straight on the chair with their hands on their thighs and their backs touching the back of the chair After they were given the 'go' signal from the tested, they arose from the chair, walked at their normal speed, they turned around right after passing the tape at the end of the pathway, returned back to the chair, turned around and sat down. The tester timed their performance with a stop-watch. All sessions were recorded on video to verify performance.

To assess test-retest reliability of the measured parameters, nine subjects in each group repeated the protocol a second time. After finishing the 3 iTUG tests, sensors were removed from their body. After one hour, the sensors were replaced, and the protocol was repeated. We assumed that the subjects' performance remained the same within this time period. The same examiner used the same device and same protocol to test the subject for the second time.

1.3 Systems and Devices

Subjects wore a small data-logger in a waist-worn pack with seven inertial sensors attached on the forearms, shanks, thighs and sternum. To limit the number of recorded channels, a different combination of accelerometers and gyroscopes was used for each body site: a sensor with a 3D accelerometer (±5 g) and a 2D gyroscope (±400°/s, yaw and pitch axes) was fixed on sternum with double stick tape. A 2D gyroscope (±1200°/s, yaw and pitch axes) was attached on each forearm and a single axis gyroscope (±600°/s, pitch axes) was placed on each thigh and shank with Velcro straps. Sampling rate was 200 Hz. The data was recorded on a 128 MB SD flash card.

1.4 iTUG Protocol Components

The TUG was divided into 4 major components: sit-to-stand, turn-to-sit, gait and turning. We extended the length of the normal TUG from 3 meters to 7 meters to increase the total number of analyzable gait-cycles. Each subcomponent of the iTUG was detected with a unique subset of sensors: sit to stand and turn to sit transitions were detected and analyzed using the trunk sensor. Steps during gait and turns were detected using the two sensors on the shanks Turns were detected using the trunk sensor and quantified using the novel method described herein.

1.5 ITUG Metrics (Outcomes)

The following outcomes were calculated for each subcomponent of iTUG. Sit-to-stands metrics: A) Average and peak angular velocity of trunk in the sagittal plane (in degrees per second). B) Duration (in seconds) and range of motion of the trunk in the sagittal plane (in degrees).

Gait metrics: A) Temporal parameters including Cadence (number of steps per minute), Stance (as percentage of gait cycle time), Double support (as percentage of gait cycle time), Limp (i.e. difference between initial and terminal double support as a percentage of gait cycle time). B) Performance of the lower limbs including Range of Motion (ROM) of shanks, thighs as well as flexion-extension of knee (all in degrees), stride-length (normalized to the stature), stride-velocity (stride-length divided by gait cycle time) and peak angular velocity of shanks (in degrees per second). C) Performance of the upper limbs including arm-swing in Pitch and Yaw axes (in degrees), peak angular velocity (by combining Pitch and Yaw axes, reported in degrees per second) and its left/right asymmetry (difference of the left and right divided by the faster one, reported as percentage). D) Performance of the trunk including ROM in horizontal and sagittal planes as well as peak angular velocity in horizontal and sagittal planes.

Turning metrics: A) Duration of turns (in seconds). B) Peak angular velocity of the trunk in horizontal plane (in degrees per seconds). C) Number of steps, average step time (from heal-strike to heal-strike, in seconds), time for the longest step (in seconds), last step time right before turn (in seconds) and number steps of double steps, i.e. successive steps with the same foot. Turn-to-sit metrics: A) Turning metrics. B) Range of motion of trunk in the sagittal plane (in degrees).

1.6 Data Analysis Mean value of the straight walking gait metrics across all 3 trials were reported. The median of metrics of the transitions and turns in the 3 trials were reported to eliminate outliers.

To compare differences between the mild PD and control groups, Wilcoxon's non-parametric test (rank-sum) was used. Since the tests for the metrics where pre-planned, the p-values were not adjusted for multiple-comparisons. To evaluate test-retest reliability of the iTUG, Intra-Class Correlation (ICC) was used. Since the same subjects and same device was used for reliability, an ICC(1,1) was used and p and 95% confidence intervals were reported.

1.7 Results of Reduction to Practice and Operation: Sensitivity and Reliability

The total time to perform the TUG was not significantly different between the early PD group and control group (15.4±0.6 vs. 14.3±0.5 seconds, p>0.18). After combining three repetitions of iTUG and removing gait cycles overlapping with turns and transitions, there was no significant difference in number of gait cycles between groups: the PD group had 15.6±3.5 gait cycles and the control group had 15.5±3.9 gait cycles (p>0.95). Table 1 shows a list of the outcome metrics. Despite the similarity of the total time to perform iTUG and the similar number of gait cycles between the two groups, several parameters related to some components of iTUG, namely gait, turns and turn-to-sit, showed significant differences between groups. The only component of iTUG that was not significantly different between the two groups was the sit-to-stand.

Temporal parameters of gait, with the exception of limp, showed an excellent reliability (p>0.90). Spatial parameters (stride-length and stride-velocity) showed somewhat lower, but yet good, reliability (p>0.75). Reliability of the estimated duration of turn and turn-to-sit transitions were also very high. Sit-to-stand parameters, however, did not show good test-retest reliability. Table 2 summarized the test-retest reliability results.

It is noteworthy that although we focused on 180° turns in this study, the mathematical model can be used to analyze turning by 90° or any other value. In fact, due to alignment of the sensor on the body turns were not exactly 180° thus as part of the fitting process, the model measures the turning angle. We hypothesize that this approach can be used to analyze turns under various other conditions, including unplanned, free turns during continuous measurement of spontaneous activity.

Gait was the most reliable subcomponent of the test. Cadence was the most reliable metric (p=0.94). Stride-length and stride-velocity showed moderate to good reliability (p=0.67 and 0.78 respectively). These findings are comparable to a recent studies. The reason that spatial parameters were less reliable than temporal might be due to the sensitivity of these measures to the alignment of the sensors on the body. There is a potential to improve the reliability of these parameters by improving the gait analysis method with 3D, instead of 1-D, gyroscopes. Limp, i.e. difference between initial and terminal double-support, was the least reliable gait measure (p=0.25) probably due to its very short duration (≈20 ms) compared to the sampling period of the system (5 ms).

Duration of turns was the most reliable turning metric. The reason might be due to the fact that the turning model uses the whole signal, including gait prior to and after the turn, and is not particularly sensitive to local noise near onset and offset of turns. The least reliable measure related to turning was the number of double steps. The relatively mild PD subjects rarely took double steps and did not need to use double steps consistently in all trials. Healthy subjects never took double steps. Reliability of the turn-to-sit metrics were comparable to the turning metrics.

The sit-to-stand component was the least reliable part of the test. This finding is similar to the findings of a previous study looking at duration of the TUG test components. The poor reliability of the sit-to-stand metrics might be due to the large degrees of freedom available to subjects who can use a variety of strategies to perform this activity, despite our efforts to limit this freedom by giving subjects explicit instructions on how to perform the test and using the same chair during all trials. Another reason for poor reliability might be due to our analysis method that relies on detection of peak angular velocity, though we have used appropriate filters to minimize the effect of noise in peak-identification.

Significant differences between the early PD and age-matched control groups could be observed in three, out of four, components of the iTUG, although the total time to perform the iTUG test was not sensitive enough to separate the groups' performance Subjects with early PD had especially slow turning, arm swing and cadence, although they performed normally in other components, including sit-to-stand and turn-to-sit.

Figure 6:
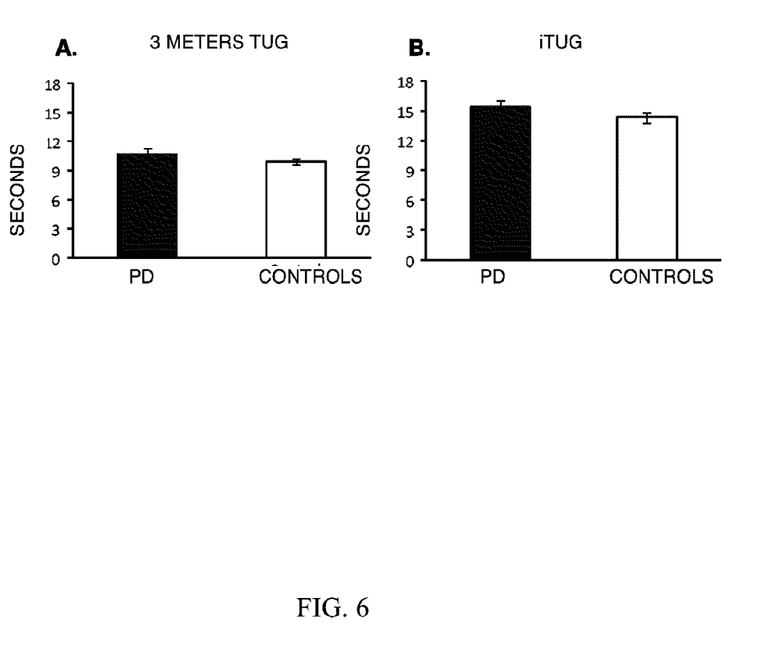
FIG. 6 shows a comparison in total performance time between untreated subjects with PD and control subjects on the traditional, 3-meter TUG test and the 6-meter iTUG test.
Figure 7:
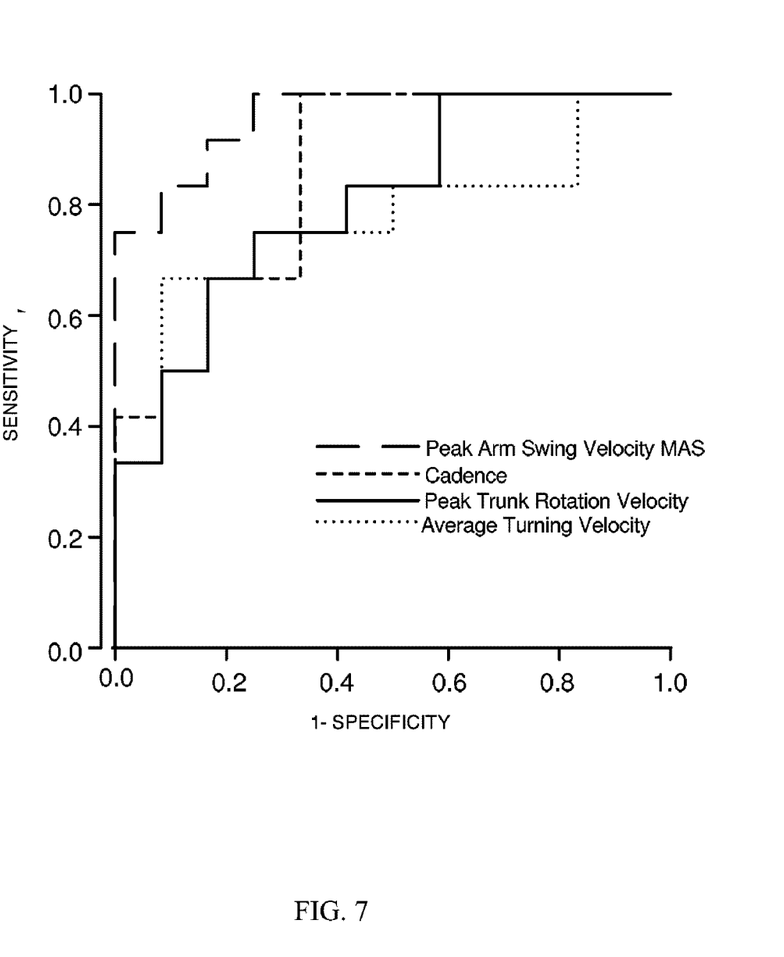
FIG. 7 shows receiver operating characteristics (ROC) curve for peak arm swing velocity of the more affected side (MAS), cadence, peak trunk rotation velocity, and average turning velocity.
Figure 8:
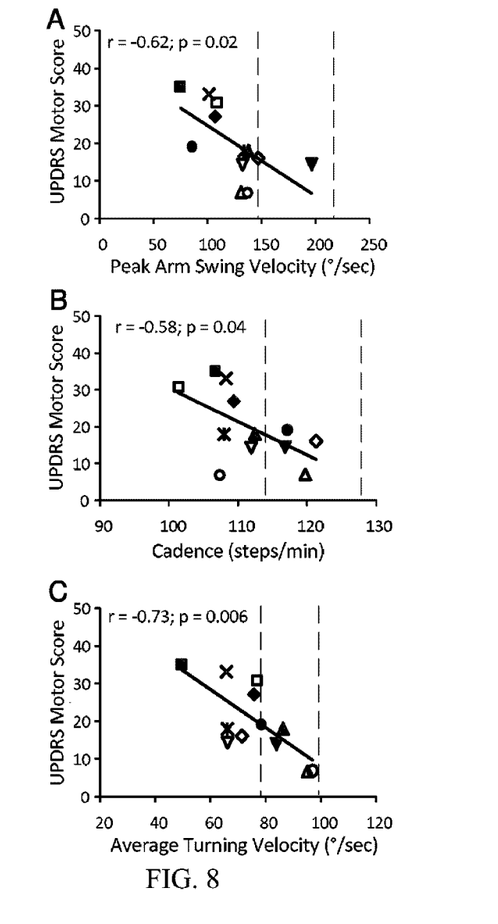
FIG. 8 shows the relationship between UPDRS Motor Scores and iTUG parameters in the PD group.
Figure 12:
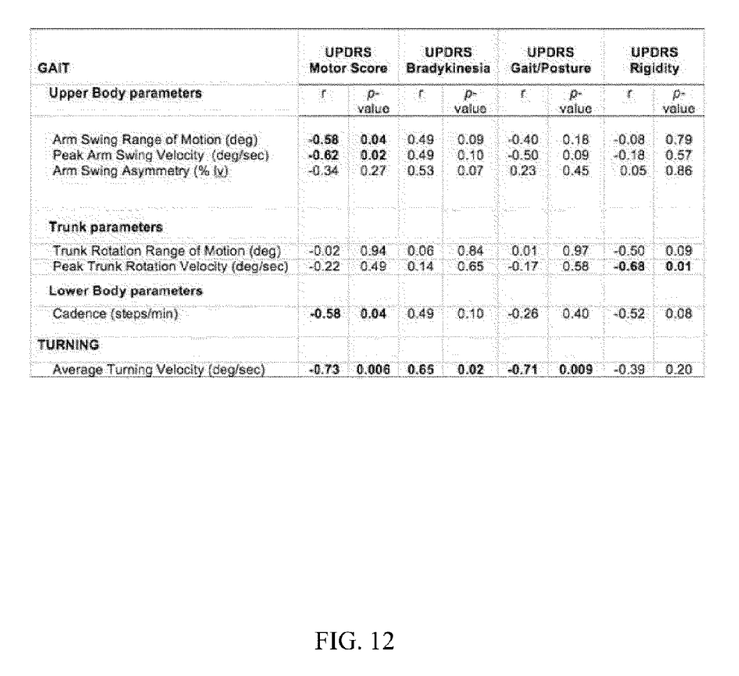
FIG. 12 shows a table containing the correlation between iTUG components and UPDRS Motor Section Scores.

FIG. 6 shows a comparison in total performance time between untreated subjects with PD and control subjects on the traditional, 3-meter TUG test and the 6-meter iTUG test. FIG. 7 shows receiver operating characteristics (ROC) curve for peak arm swing velocity of the more affected side (MAS), cadence, peak trunk rotation velocity, and average turning velocity. FIG. 8 shows the relationship between UPDRS Motor Scores and iTUG parameters in the PD group. FIG. 9 shows a table containing sample iTUG outcome results grouped by type of activity. FIG. 10 shows a table containing sample test-retest reliability of the proposed iTUG metrics. FIG. 11 shows a table containing the gait and postural transition parameters obtained with the proposed iTUG test. FIG. 12 shows a table containing the correlation between iTUG components and UPDRS Motor Section Scores.

While particular embodiments have been described, it is understood that modifications and generalizations will be apparent to those skilled in the art without departing from the spirit of the invention. Those skilled in the art will appreciate that alternative actual reductions to practice and implementations of the proposed mobility assessment system (iTUG) are possible without departing from the spirit of the invention.

What is claimed is:

1. A system for assessing onset and offset of turns by a moving subject to objectively quantify movement of the subject:
(a) a plurality of wearable sensors operable to collect kinematics data obtained from the subject, wherein at least one sensor is configured to be located on a trunk of the subject and is operable to receive a trunk angle signal in a horizontal plane from the subject; and
(b) a computing device operable to receive the kinematics data, wherein the computing device is further operable to describe the trunk angle signal using a continuous piecewise mathematical model, estimate coefficients of the continuous piecewise mathematical model using estimation methods, wherein the coefficients represent amplitude, time and duration of turns, fit the continuous piecewise mathematical model having estimated coefficients to the kinematics data received using numerical optimization to create a fit continuous piecewise mathematical model; and determine onset and offset of turns of the subject from the fit continuous piecewise mathematical model.

2. The system according to claim 1, wherein the computing device is further operable to determine a coefficient of determination for the fit continuous piecewise mathematical model, wherein the coefficient of determination represents the quality of fit of the fit continuous piecewise mathematical model to the kinematics data.

3. A computer-implemented method for assessing onset and offset of turns by a moving subject to objectively quantify movement of the subject, comprising:
obtaining, by a computing device operably coupled to a plurality of wearable sensors on the subject, from the plurality of wearable sensors, kinematics data, wherein at least one sensor is located on a trunk of the subject and is operable to receive a trunk angle signal in a horizontal plane from the subject;
describing, by the computing device, the trunk angle signal using a continuous piecewise mathematical model;
estimating, by the computing device, coefficients of the continuous piecewise mathematical model using estimation methods, wherein the coefficients represent amplitude, time and duration of turns;
fitting, by the computing device, the continuous piecewise mathematical model having estimated coefficients to the kinematics data using numerical optimization to create a fit continuous piecewise mathematical model; and
determining, by the computing device, onset and offset of turns of the subject from the fit continuous piecewise mathematical model.

4. The computer-implemented method according to claim 3, further comprising determining, by the computing device, a coefficient of determination for the fit continuous piecewise model, wherein the coefficient of determination represents the quality of fit of the fit piecewise continuous model to the kinematics data.

5. The system according to claim 1, wherein the at least one sensor is configured to be located on a sternum of the subject.

6. The system according to claim 5, wherein the at least one sensor is a yaw gyroscope.

7. The system according to claim 5, wherein the at least one sensor is configured to determine a particular angle of a turn.

8. The computer-implemented method according to claim 3, further comprising placing the at least one sensor on a sternum of the subject.

9. The computer-implemented method according to claim 8, wherein the at least one sensor is a yaw gyroscope.

10. The computer-implemented method according to claim 8, wherein the at least one sensor located on the sternum of the subject is configured to determine a particular angle of a turn.

11. The system according to claim 1, wherein the computing device is further operable to integrate raw data from the at least one sensor located on the trunk of the subject to obtain a relative trunk angle signal.

12. The system according to claim 1, wherein the continuous piecewise mathematical model comprises the following equation:

$$M(t) = a_1 E\left(\frac{t-b_1}{c_1}\right) + a_2 E\left(\frac{t-b_2}{c_2}\right) + C - t$$

wherein $a_i$, $b_i$ and $c_i$ comprise the coefficients that represent the amplitude, time and duration of a turn i, respectively, wherein a, b, c and i are positive integers and t is an integer.

13. The computer-implemented method according to claim 3, further comprising integrating, by the computing device, raw data obtained from the at least one sensor located on the trunk of the subject to obtain a relative trunk angle signal.

14. The computer-implemented method according to claim 3, wherein the continuous piecewise mathematical model comprises the following equation:

$$M(t) = a_1 E\left(\frac{t-b_1}{c_1}\right) + a_2 E\left(\frac{t-b_2}{c_2}\right) + C - t$$

wherein $a_i$, $b_i$ and $c_i$ comprise the coefficients that represent the amplitude, time and duration of a turn i, respectively, wherein a, b, c and i are positive integers.

* * * * *